United States Patent [19]
Lindahl et al.

[11] Patent Number: 6,076,521
[45] Date of Patent: Jun. 20, 2000

[54] DOSE INDICATING DEVICE

[75] Inventors: Jan-Eric Lindahl, Lund; Kjell Wetterlin, Södra Sandby, both of Sweden

[73] Assignee: Astra Aktiebolag, Sodertalje, Sweden

[21] Appl. No.: 08/652,555

[22] PCT Filed: Nov. 29, 1995

[86] PCT No.: PCT/SE95/01426

§ 371 Date: Jun. 7, 1996

§ 102(e) Date: Jun. 7, 1996

[87] PCT Pub. No.: WO96/16687

PCT Pub. Date: Jun. 6, 1996

[30] Foreign Application Priority Data

Nov. 29, 1994 [SE] Sweden .................................. 9404140

[51] Int. Cl.$^7$ .................................................. A61M 15/00
[52] U.S. Cl. .............................. 128/203.15; 128/200.23
[58] Field of Search ..................... 128/203.15, 200.14, 128/200.23, 200.22, 203.12, 203.21; 222/36, 402.13; 116/311, 312, 307, 317, 318

[56] References Cited

U.S. PATENT DOCUMENTS

| | | | |
|---|---|---|---|
| 4,668,218 | 5/1987 | Virtanen ............................. | 128/203.15 |
| 5,331,953 | 7/1994 | Andersson et al. ................ | 128/200.14 |
| 5,421,482 | 6/1995 | Garby et al. ............................. | 222/36 |
| 5,505,195 | 4/1996 | Wolf et al. ......................... | 128/203.15 |
| 5,740,792 | 4/1998 | Ashley et al. ............................. | 116/317 |
| 5,829,434 | 11/1998 | Ambrosio et al. ................. | 128/203.15 |

FOREIGN PATENT DOCUMENTS

| | | |
|---|---|---|
| 466684 | 3/1992 | Sweden . |
| 2 265 552 | 10/1993 | United Kingdom . |
| WO 90/10470 | 9/1990 | WIPO ............................... 128/203.15 |
| WO 91/06334 | 5/1991 | WIPO ............................... 128/200.14 |
| WO 94/12230 | 6/1994 | WIPO . |
| WO 94/14492 | 7/1994 | WIPO ................................... 116/317 |

OTHER PUBLICATIONS

PCT International Search Report.
PCT International–Type Search Report (4 pages).

*Primary Examiner*—Aaron J. Lewis
*Assistant Examiner*—Teena Mitchell
*Attorney, Agent, or Firm*—Fish & Richardson P.C.

[57] ABSTRACT

A dose indicating device constructed for use with an inhalator is disclosed. The inhalator contains multiple doses of a medicament and has an operational portion that includes a dosing unit defining an inhalation channel, and a maneuvering element. The maneuvering element loads a dose of the medicament to the dosing unit and provides the dose in a position in the inhalation channel for inhalation. The dose indicating device includes: a body constructed to be mounted on the maneuvering element of the inhalator; a first element constructed to be mounted on and around an outer wall surface of the maneuvering element; a second element rotatably mounted on and around the outer surface of the first element for rotation relative to the first element; corresponding portions provided on the first and second elements constructed to engage when the inhalator is activated for inhalation in a manner to limit relative movement between the first and second elements; and an indicator constructed to detect movement of the maneuvering element and indicate to a user of the inhalator that a dose has been fed to the inhalation channel when the inhalator is activated for inhalation.

17 Claims, 7 Drawing Sheets

DOSE INDICATING DEVICE

FIELD OF INVENTION

The present invention relates to a dose indicating device intended to be provided on an inhalator, preferably a breath-actuated dry-powder inhalator, designed for multiple doses of a medicament containing an active substance, the inhalator having operating means comprising a maneuvering element for loading one dose of the medicament to a dosing unit and providing said dose in a position for inhalation as described in the first part of claim 1.

BACKGROUND OF THE INVENTION

Today most multi dose inhalators used for treatment of diseases in the bronchial area have no dose indicating device or have a device only indicating when the storage compartment is empty.

There is a strong desire among the users of such inhalators, patients as well as treating doctors and especially among parents having children using dry powder inhalators, that the inhalators should be provided with dose a indicating device indicating each and every dose as well as the number of doses fed from the storage of the medicament in order to be able to see how many doses are left in the inhalator. This could also be used to determine how many doses have been fed during a certain period of time in order to establish the correct form of therapy.

PRIOR ART

In the multi dose breath-actuated dry-powder inhalator of the type described schematically in EP-A-0 069715 and EP-A-0 237 507 and sold under trademark Turbuhaler®, a dose indicating device has been built into the construction. This dose indicating device indicates both when 20 doses of the medicament are left in the storage chamber of the inhalator and when no medicament for inhalation is left. This indicating device is described in EP-A-0 258 238.

For this type of inhalator there has also been constructed a dose indicating device indicating every 25th dose until there are only 20 doses left and an indication of every 5th dose thereafter. Such a device can be seen in WO SE93/00389.

The known devices are all more or less inaccurate and do not provide a dose indicating system where each and every dose fed is indicated and/or registered. Furthermore all known indicating devices provided in such inhalators are not only complicated to produce in themself but also make the hole production of the inhalators more complicated. Such devices are also expensive and take a lot of space within the inhalators.

THE INVENTION

The present invention is set out to provide a dose indicating device which solves the above mentioned problems.

According to the invention there is provided a dose indicating device which is provided as a separate unit to be placed on the maneuvering element of the inhalator. The dose indicating device comprises a first element to be provided on and around the maneuvering element, a second element provided on and around the outer surface of said first element, said second element being rotatable relative to said first element, interrupting means provided on said first and second elements limiting the length of the relative movement between said elements, and registration/indication means for registration of the movement of the maneuvering element and thereby the feeding of a dose to the inhalation channel when the inhalator is activated for inhalation said registration/indication means being provided as parts of said first and second elements as described in the characterising part of claim 1.

As every turning of the maneuvering element, and thereby the dosing unit, will move a dose in the dosing unit from the position where it is loaded into the dosing unit to a position in the inhalation channel ready for inhalation the construction of the dose indicating means as described in claim 1 will register and indicate each and every dose activated for inhalation. The device is also easy to manufacture, to mount on the maneuvering element of the inhaler and to use for the patient.

The dose indicating device is thereby constructed as a unit to be placed on the maneuvering element of the operating means of an inhalator of the above mentioned type. If preferred it can thereby be releasably mounted to be removed after the inhalator has been emptied and placed on a new inhalator.

The device according to the invention provides a device which is accurate and which registers and indicates each and every dose moved into position for inhalation in the inhalation channel. It is constructed in a manner which makes it flexible in its construction as it can easily be modified to different demands and requirements, easy to manufacture and easy to use.

The two main parts of the device, the first and second elements are preferably formed as cylinders. A display opening for displaying the number of the actual dose placed in the inhalation channel is provided on the second element.

The interrupting means preferably comprise lugs and holes provided on the outer surface of the first element and on the inner surface of the second element respectively and arranged to co-act with each other when the maneuvering operating means of the inhalator is activated for inhalation.

The registration/indication means could either be mechanical or electronical.

Mechanical registration/indication means could have different constructions. In one embodiment the device comprises a digit wheel and a gear wheel provided in the second cylinder and a driving arm provided on the inner wall of the first cylinder, said driving arm pushing the teeth of the gear wheel one step thereby turning the digit wheel in order to move a new digit into display position in the display opening of the second cylinder when the maneuvering element and thereby the first cylinder is rotated.

It could also comprise a digit tape provided on at least one roller having a gear wheel provided in the first cylinder and a driving arm provided on the inner wall of the second cylinder, said driving arm pushing the teeth of the gear wheel one step thereby turning the roller with the digit tape in order to move a new digit into display position in the display opening in the second cylinder when the maneuvering element and thereby the first cylinder is rotated.

Another possible modification of a mechanical registration/indication device comprises a digit disc having a driving wheel with steps and a driving arm provided on the inner wall of the first cylinder, said driving arm pushing the steps of the driving wheel one step thereby turning the digit disc in order to move a new digit into display position in the display opening in the second cylinder when the maneuvering element and thereby the first cylinder is rotated.

In this embodiment a guiding path along which the digits are provided and in that an aperture disc is provided adjacent said digit disc whereby a magnifying device is provided in the aperture of the aperture disc and moving along the guiding path when the cylinders are moved relative to each other.

The registration/indication device could also comprise a gear wheel being fixed to the first cylinder, and an inner and an outer digit disc being provided with teeth, whereby the teeth of the gear wheel co-acts with the teeth of the inner digit disc and moves it in relation to the outer disc whereby a new digit will be moved into display position in the display opening when the maneuvering element and thereby the first cylinder is rotated.

Here the inner and outer discs are preferably provided with inner and outer digit discs with digits of hundreds and tens and the units digits in order to make it possible to register 199 doses.

In the embodiment including an electronical registration/indication device the means for indicating the number of the dose positioned in the inhalation is a circuit board comprising a microphone, a battery, a microprocessor and a microswitch.

In this embodiment the microphone detects a click-sound which is created when the maneuvering element is rotated, in that the first cylinder is provided with a lug which activates the microswitch when the cylinder is rotated and in that said sound impulse from the microphone and the impulse from the microswitch activates the microprocessor which will display a new digit in the display opening.

Indications, preferably as marks, are provided on the housing and the maneuvering element of the inhalator or the first element of the registration/indication device to be used to indicate whether the maneuvering element and thereby the first element have been rotated to their stop limits when the inhalator has been activated for inhalation.

The registration/indication device according to the invention is intended to be used in connection with an inhalator. It is intended to be placed on the inhalator which preferably is a dry powder breath-actuated multi dose inhalator, most preferably of the type sold under the trademark Turbuhaler®

BRIEF DESCRIPTION OF THE INVENTION

The dose indicating device according to the present invention will now be described by way of example with reference to the appended drawings, wherein.

DETAILED DESCRIPTION OF THE DRAWINGS

Figure 10:
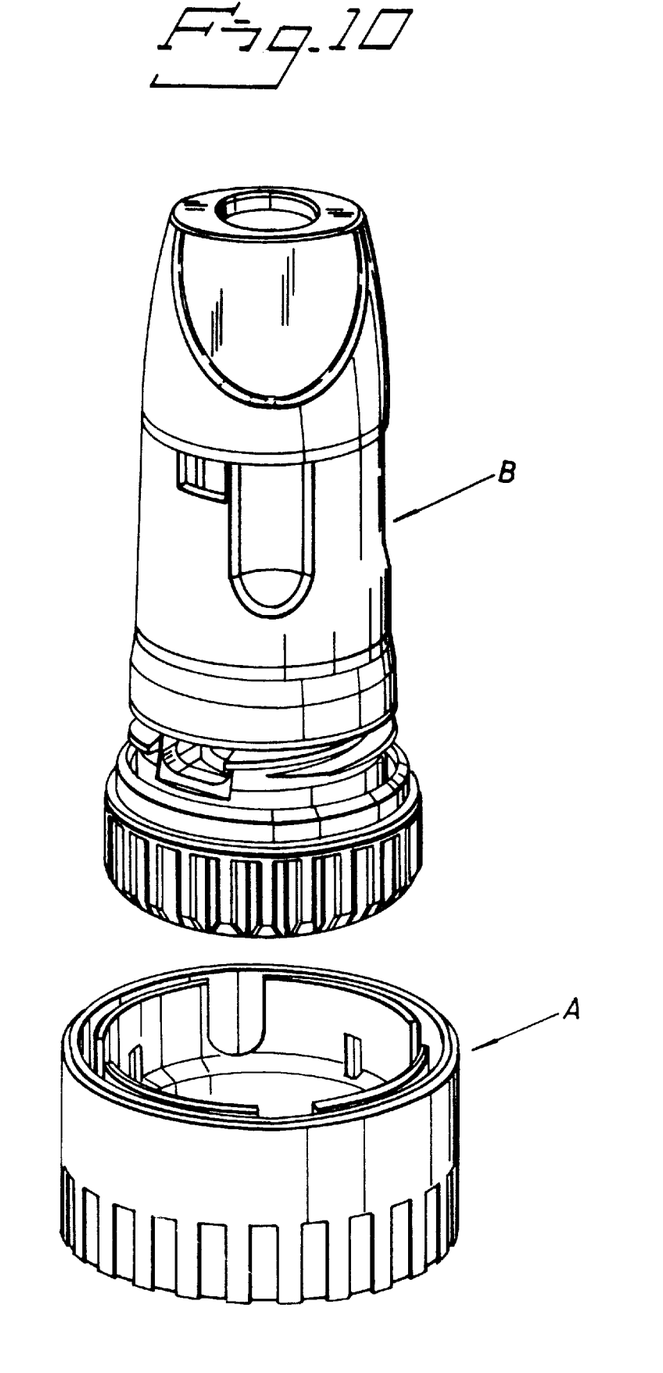
FIG. 10 shows a inhalator of the preferred type and a dose indicating device according to the invention.

The device according to the invention is intended to be used in connection with an inhalator, e.g. the breath-actuated dry-powder multi dose inhalator registered and sold under the name Turbuhaler®. The indicating device could naturally be modified within the scope of the appended claims to be used with any dry-powder inhalator which when activated places a dose of the medicament in an inhalation channel. The preferred inhalator is provided with operating means comprising a maneuvering element A, shown in FIG. 10 only, which, when rotated by the user, moves a dosing unit from a loading position in which a predetermined dose of the medicament is metered into the dosing unit and an inhalation position where the dose is placed in the inhalation channel, released and carried by the inhalation air through the channel to a mouthpiece and to the user. The rotation of the maneuvering element, and thereby the dosing unit, is carried out in two directions, each rotation being limited by stop means. The Turbuhaler® and its function is described in EP-A-0 069 715 and EP-A-0 237 507, see also FIG. 10.

In order to protect the inhalator from humidity and contamination it is provided with a cap (not shown).

The main construction of the dose indicating device according to the invention is to be seen in FIGS. 1 to 9 and comprises a first element in the form of a cylinder 1 having a bottom plate. This first element or cylinder is adapted to fit on the maneuvering element A of the inhalator and follows the movement of said maneuvering element when this is rotated. The first cylinder could be applied on the maneuvering element A by press fitting or any other method such as screwing, by using a bayonet fitting or by using any kind of male-female connection, i.e. by providing pins on one part which connects to corresponding holes in the other part. On the outer surface of the first cylinder lugs 3 are provided.

A second element 2 is provided and has the form of a second cylinder. The inner diameter of said second cylinder is just slightly greater than the outer diameter of the outer surface of the first cylinder in order to be provided around the outer surface of the first cylinder 1 whereby said second cylinder is movable tangential and relative to the first cylinder 1.

Openings 4 which preferably are oblong are provided on the walls of the second cylinder 2. When the second cylinder is placed on to the first cylinder the lugs 3 will enter into the oblong openings 4. The openings 4 permits the lugs 3 to move a predetermined path when the cylinders are moved relative to each other thereby limiting the movement. The second cylinder could be spring loaded in relation to the first cylinder.

In order to prevent an accidental turning of the maneuvering element in the embodiments having mechanical dose indicating devices and thereby a registering of a fed dose when the cap of the inhalator is screwed on or off the main body of the inhalator a locking ring 9 may be connected with the first cylinder 1. This locking ring 9 is pressed downwards by the cap when it is screwed on to the inhalator thereby locking the first 1 and second 2 cylinders from moving relative to each other.

Figure 1:
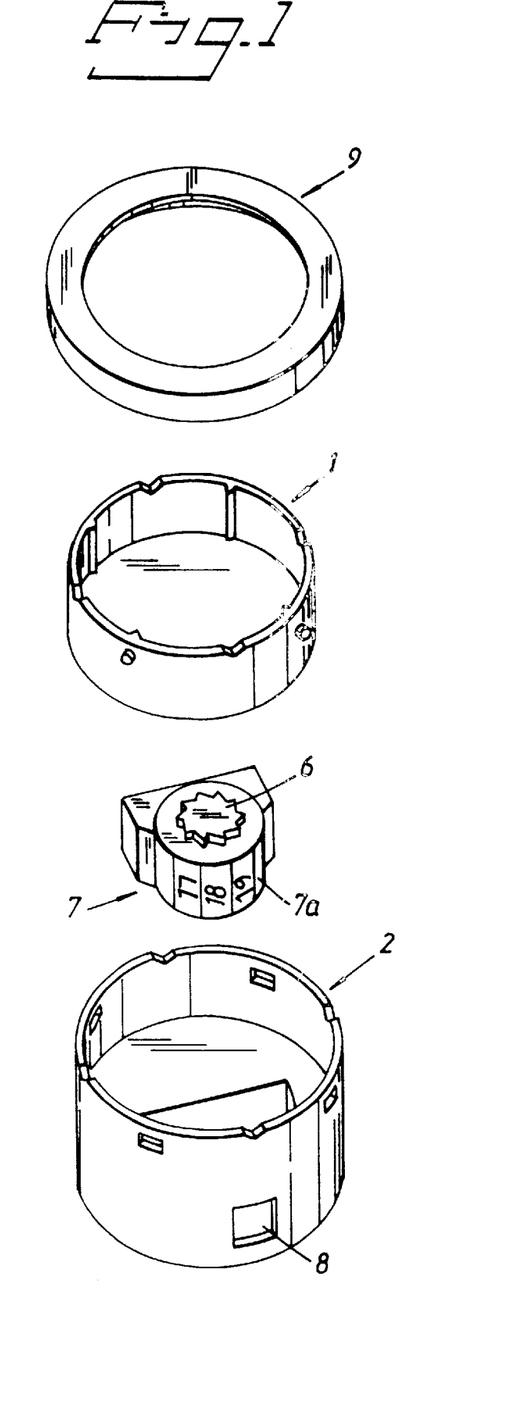
FIGS. 1 and 2 are elevational views of a first preferred embodiment of the invention.
Figure 2:
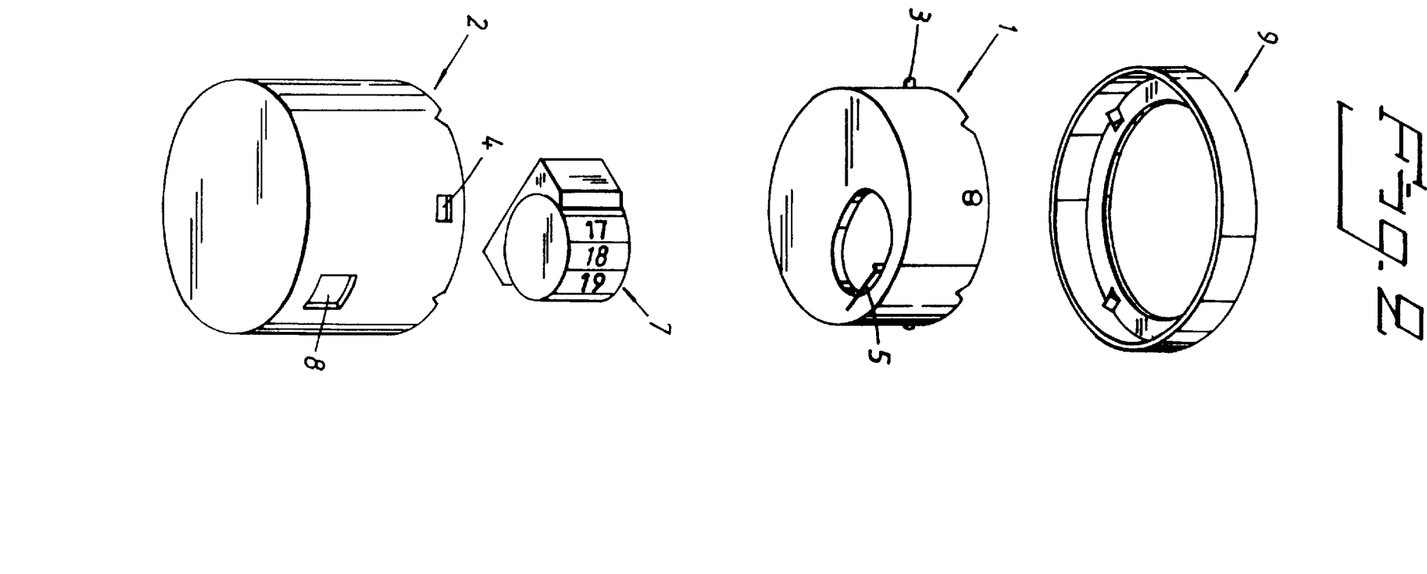

In the first embodiment mechanical dose indicating means are provided within the second cylinder, as can be seen in FIGS. 1 and 2. A driving arm 5 is provided in the bottom of the first cylinder 1. A registering and indicating unit 7 with a digit wheel 7a is provided in the second cylinder 2. A display window 8 is also provided in the second cylinder in which the numbers of the digit wheel are displayed. When the cylinders 1 and 2 are moved relative to each other the driving arm 5 co-acts with a gear wheel 6 provided on the digit wheel 7 turning the digit wheel one step and a new number corresponding to the number of the dose placed in the inhalation channel is displayed through the display window 8.

Figure 3:
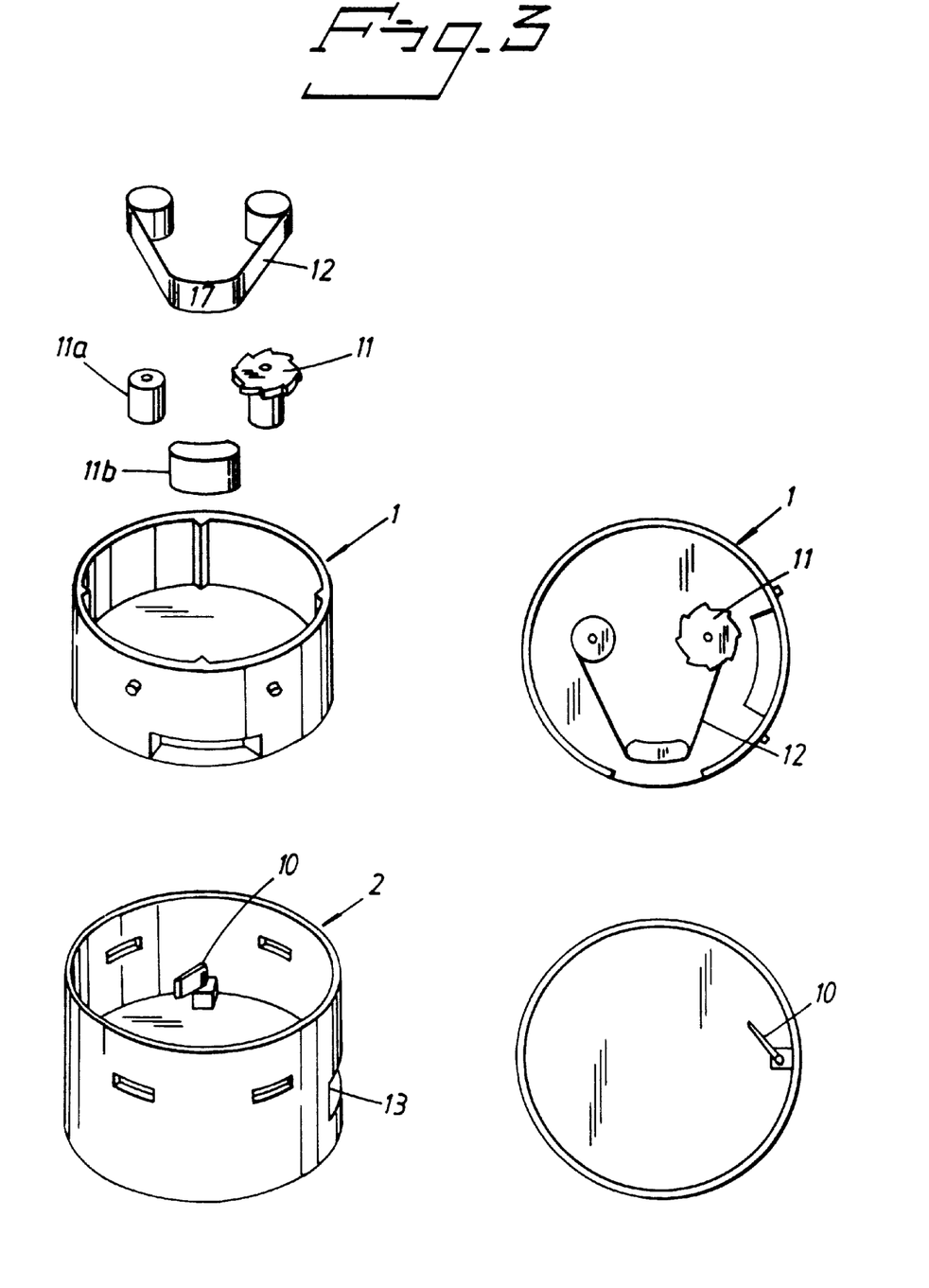
FIG. 3 is an elevational view of a second preferred embodiment of the invention.

A second embodiment of the dose indicating device is to be seen in FIG. 3.

In this embodiment the main construction of the device corresponds to the construction described in relation to the first embodiment. The first and second cylinders are provided in the same manner but the indicating unit is provided as a tape with digits placed in the first cylinder 1. A driving arm 10 is provided on the inner wall of the second cylinder 2 and co-acts with a gear wheel 11. The gear wheel 11 is provided on a roller on to which the digit tape 12 is provided at its one end. The other end of the digit tape 12 is provided on a second roller 11a. A guiding element 11b is provided between the two rollers 11 and 11a as can be seen in FIG. 3. When the cylinders are moved relative to each other during the turning of the maneuvering element A the driving arm 10 moves the gears of the wheel 11 and the tape moves one step forward. A display window 13 is provided in the wall of the second cylinder 2 where the digits of the tape corresponding to the number of the dose are displayed.

Figure 4:
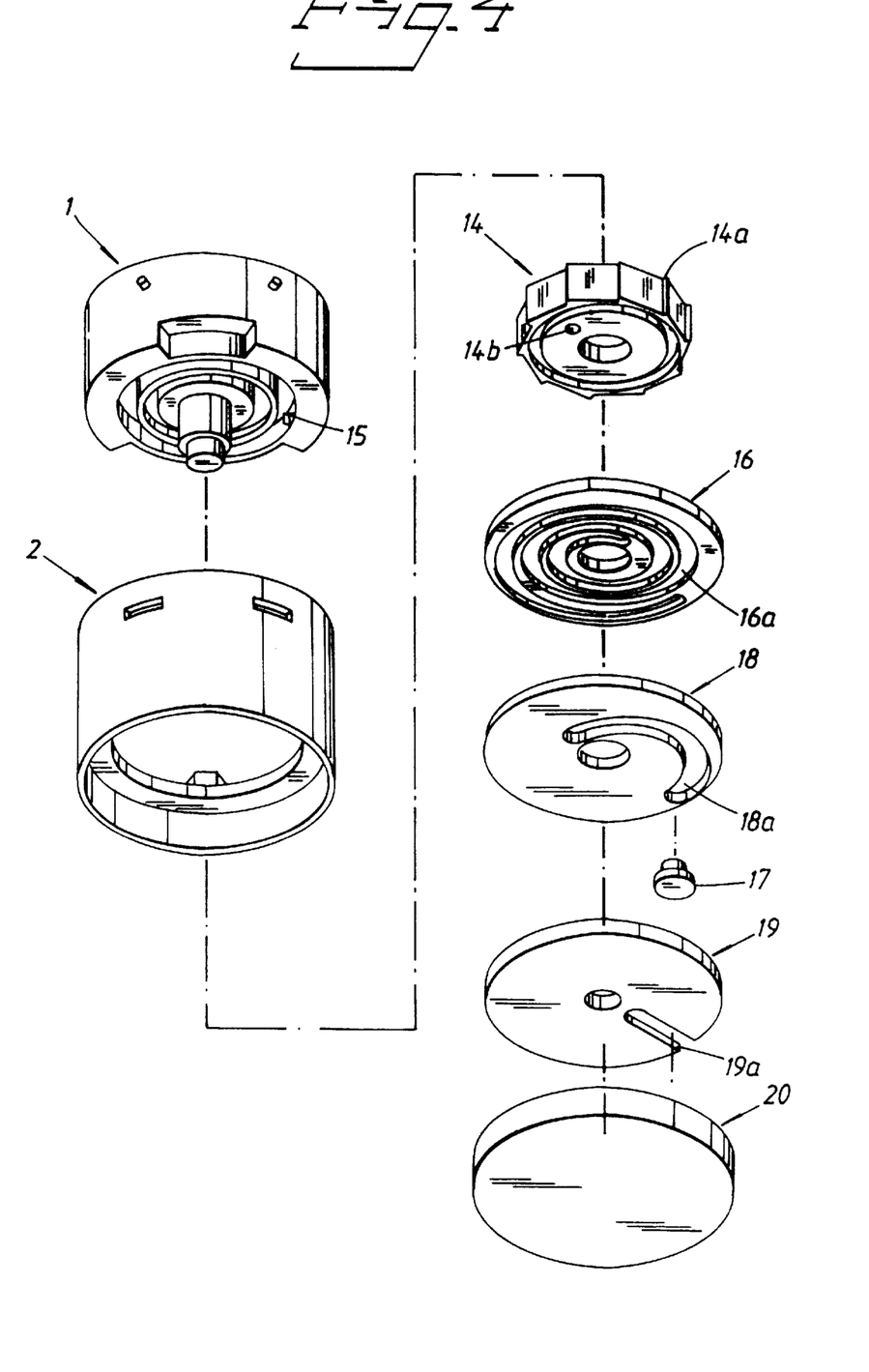
FIGS. 4 and 5 are elevational views of a third preferred embodiment of the invention.
Figure 5:
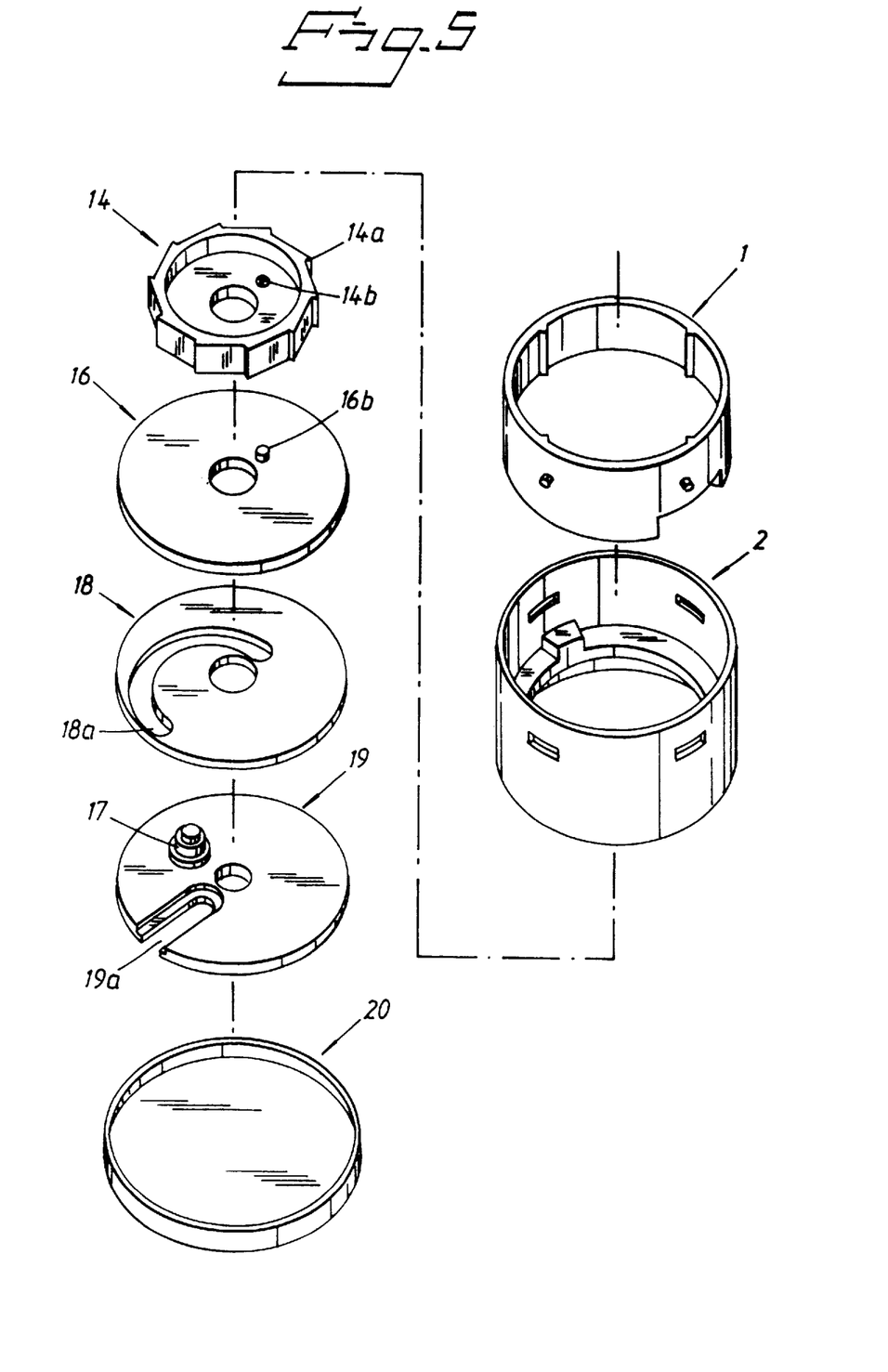

In FIGS. 4 and 5 a third embodiment of the invention is disclosed. The main construction of the dose indicating device according to this embodiment corresponds to the construction described in relation to the first embodiment. A driving arm 15 is provided in the bottom plate of the first cylinder 1. The bottom plate of the first cylinder 1 is provided with a shaft protruding into the second cylinder 2. The indicating means comprises a driving wheel 14 with steps 14a and a hole 14b, a digit disc 16 having a lug 16b, an aperture disc 18, a magnifying device 17 and a covering disc 19. The digit wheel 16 has a spiral formed guiding path 16a along which the digits are provided.

When the dose indicating device according to this embodiment is assembled the driving wheel 14 is placed on to the shaft of the first cylinder in such a manner that the driving arm 15 co-acts with the teeth 14a. The digit disc 16 is provided with said lug 16b protruding into the hole 14b of the driving wheel. The aperture disc 18 is placed adjacent the digit disc 16 and the magnifying device 17 is Placed in the aperture 18a of the aperture disc. The covering disc 19 is provided with a display opening 19a into which the magnifying device 17 is placed. A transparent bottom plate 20 is placed in the second cylinder and the fu-st and second cylinders are joined together in the above mentioned manner. When the maneuvering element A of the inhalator is rotated the driving arm 15 of the first cylinder moves the driving wheel 14 one step whereby the digit disc 16 is moved one step. The magnifying device 17 is provided in the spiral formed path 16a of the digit disc where the digits are placed and when the cylinders move relative to each other a new digit will enter into the area of the magnifying device 17 and can be seen through display opening 19a in the covering disc 19 and the transparent bottom plate 20.

Figure 6:
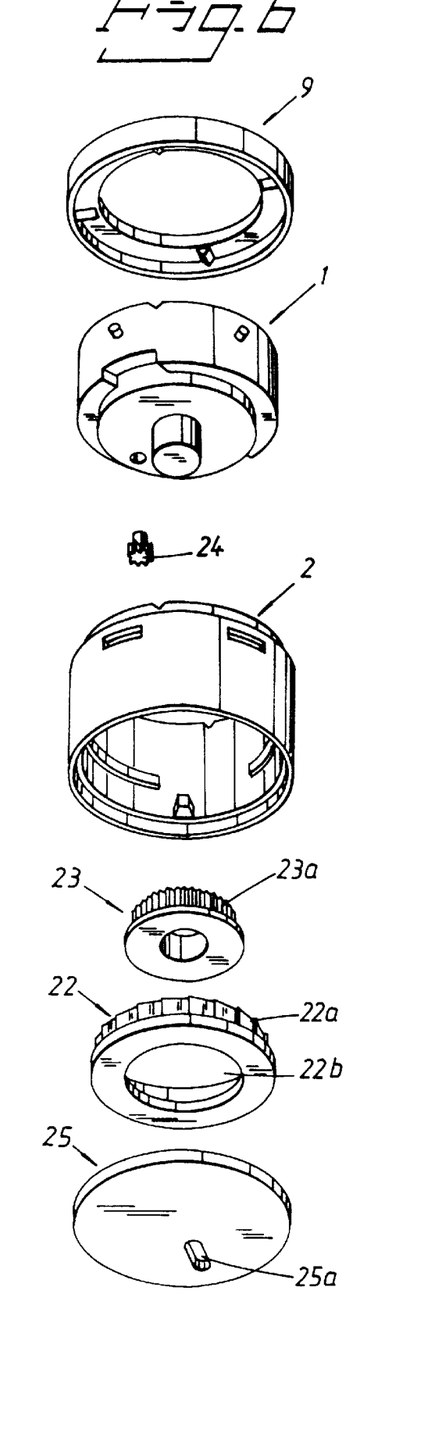
FIGS. 6 and 7 are elevational views of a fourth preferred embodiment of the invention.
Figure 7:
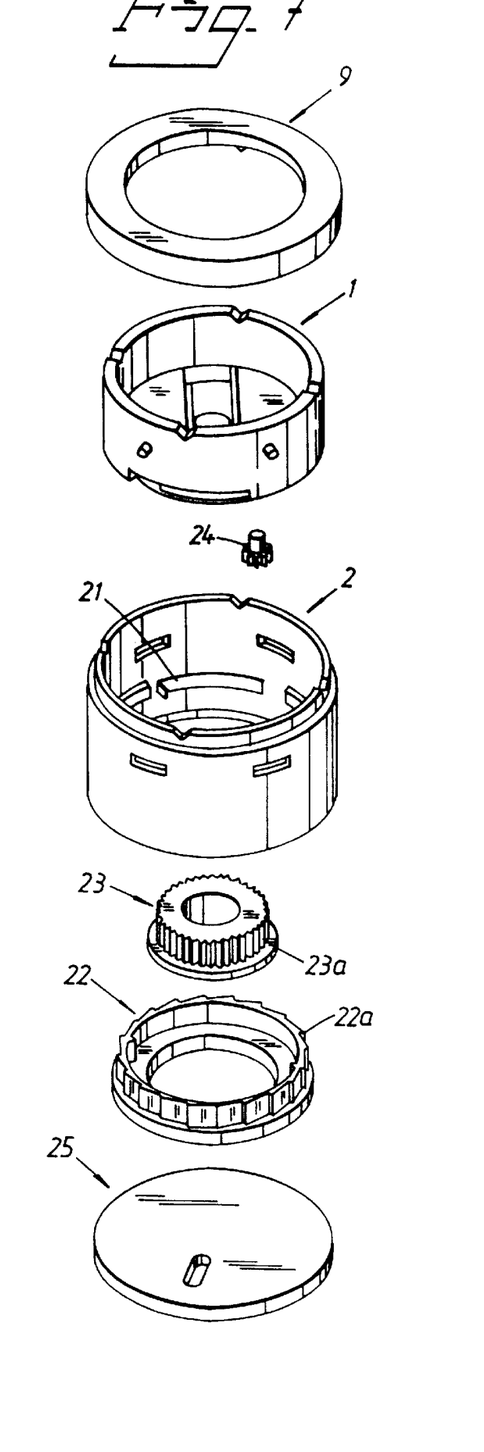

FIGS. 6 and 7 disclose a further embodiment of the invention where the main construction of the dose indicating device is the same as in the above described embodiments. As can be seen in FIG. 6 the bottom plate of the first cylinder 1 is provided with the protruding shaft. The means for indicating and registering the doses comprises a gear wheel 24, an inner digit disc 23 and an outer digit disc 22 having a bottom part with an annular opening 22b. The gear wheel 24 is mounted in a hole in the bottom plate of the first cylinder. The inner digit disc 23 is mounted on the protruding shaft and is provided with teeth which co-act with the gear wheel 24. The outer digit disc 22 is provided with teeth 22a and mounted in the second cylinder in such a manner that a driving arm 21 provided in the second cylinder co-acts with the teeth of the outer digit disc 22. The digits are provided on the bottom part of the digit discs in a manner which will be described below. The number of the dose fed is displayed through a display window 25a in the bottom plate 25 of the second cylinder 2.

The relative movement between the first and the second cylinder is transmitted via the driving arm (21) to the outer digit disc (22). The gear wheel (24) transmits the movement to the inner digit disc (23). Due to the marking of the discs a high amount of doses could be registered and indicated.

The digits are provided along the periphery of the bottom part of each digit ring. When assembled together the inner disc 23 will be placed inside the outer disc and the digits of the inner disc 23 will be seen in the annular opening 22b of the bottom part of the outer ring 22. In the preferred embodiment the outer digit disc has a marking of 0–9 on one half of the disc and a marking of 0–9 on the other half. The inner digit disc (23) has the marking of 00–19. When the 10th dose is activated and moved into position for inhalation the second 0 on the outer digit disc will be displayed in a display window (25a) in the bottom plate. At the same time a tooth is affected on the inside of the outer digit disc (22) by the gear wheel (24) thereby turning the inner disc (23) from 00 to 01. At doses 11 to 19 only the outer disc is affected. At dose number 20 a 0 will be displayed on the outer disc and at the same time a tooth on the inner surface of this disc will turn the inner disc 22 from 01 to 02.

Figure 8:
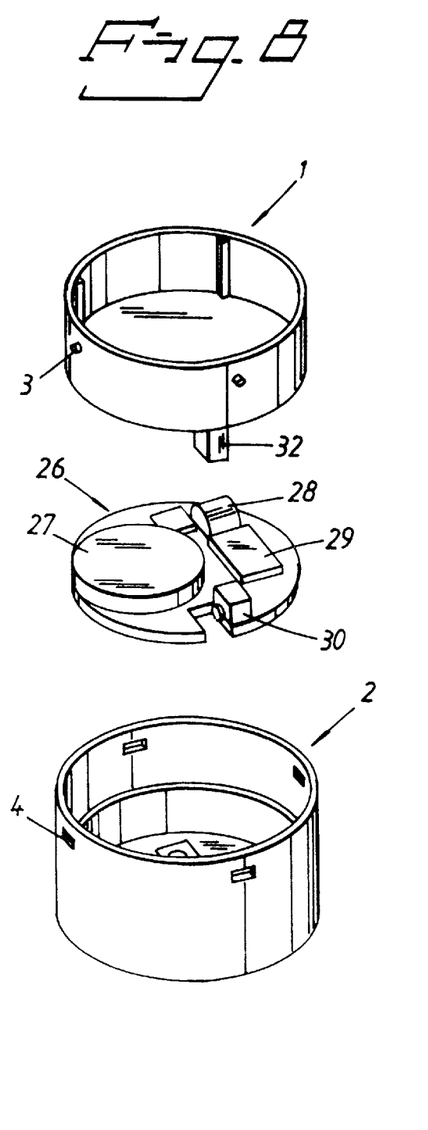
FIGS. 8 and 9 are elevational views of a fifth preferred embodiment of the invention.
Figure 9:
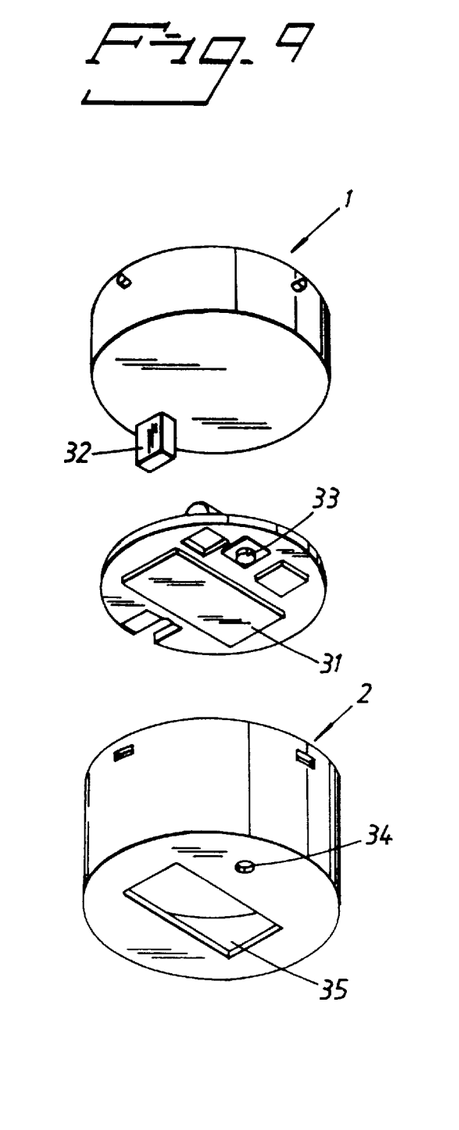

A fifth embodiment of the present invention is to be seen in FIGS. 8 and 9. This embodiment discloses a dose indicating device in which the registering and indicating means are electronic. This device provides for a certain registration of other parameters as well, such as for example a registration of the time intervals between the activation of the maneuvering element.

The main parts of the device are the same as described above, e.g. a first cylinder 1 constructed to be placed on the maneuvering element of an inhalator and a second cylinder 2 provided around the first cylinder and movable relative to it. The movement is limited by lugs 3 on the outer surface of the first cylinder and by oblong openings 4 in the walls of the 5 second cylinder.

The registration and indicating means are provided as parts on a circuit board 26 and comprises a battery 27, a microphone 28, a microprocessor 2), a microswitch 30, a display 31 and a register selector 33. The bottom plate of the first cylinder is provided with a lug 32 and the bottom plate of the second cylinder is provided with a display window 35 and an opening 34 for the register selector 33.

When the maneuvering element of the inhalator is moved to the position where the dose is fed to the dosing unit a click-sound is created in the maneuvering element. This click-sound is registered by the microphone 28. When the maneuvering element A and thereby the dosing unit are moved to the position for inhalation the microswitch 30 is affected by the lug 32 of the first cylinder. The sound impulse from the microphone 28 and the electrical impulse from the microswitch 30 must be registered by the microprocessor 29 before the dose indication will be seen in the display 31.

This electronic registering and indicating device provides a possibility to register different data such as the total amount of doses taken from the inhalator or the number of doses remaining as well as the time from the last dose or the total amount of doses taken during a specific time period, e.g. a week or similar. The register selector 33 makes it possible to change between different registers in the microprocessor which gives the doctor and the patient possibility to a more complete registration of the patient compliance in order to optimise the treatment. It is possible to provide separate sets for resetting different registers to their initial positions.

In order to facilitate for the user of the inhalator that the maneuvering element and thereby the dosing unit and the first element of the registration/indication device have been rotatated the required path to move a loaded dose to its position in the inhalation channel indications could be provided. Such indications are preferably provided as marks on the outer surface of the housing and the maneuvering element of the inhalator or on the housing of the inhalator and the first element of the registration/indication device. The indications are thereby provided to indicate the stop limits of the rotation in both directions.

Possible modifications

The dose indicating device according to the present invention could of course be modified within the scope of the appended claims.

In the preferred embodiments the first and second elements are cylinder formed but they could have any other suitable form. The different parts of the device according to the invention is preferably made of palstics or composite materials but any other material could be used.

As already mentioned above the device is desgned to be used in connection with a dry-powder breath actuated multi-dose inhalator of the kind sold under the trademark Turbuhaler® but could easily be modified within the scope of the claims to be used with any other dry powder inhalator having a maneuvering unit which is rotated when the inhalator is activated for inhalation.

What is claimed is:

1. A dose indicating device constructed for use with an inhalator containing multiple doses of a medicament, the inhalator having an operational portion comprising a dosing unit defining an inhalation channel, and a maneuvering element for loading a dose of the medicament to the dosing unit and providing the dose in a position in the inhalation channel for inhalation, said dose indicating device comprising:

a body constructed to be mounted on the maneuvering element of the inhalator;

a first element constructed to be mounted on and around an outer wall surface of the maneuvering element;

a second element rotatably mounted on and around the outer surface of said first element for rotation relative to said first element;

corresponding portions provided on said first and second elements constructed to engage when the inhalator is activated for inhalation in a manner to limit relative movement between said first and second elements; and an indicator constructed to detect movement of the maneuvering element and indicate to a user of the inhalator that a dose has been fed to the inhalation channel when the inhalator is activated for inhalation.

2. The dose indicating device of claim 1 wherein said first and second elements are cylindrical and said second element is provided with a display opening.

3. The dose indicating device of claim 2 wherein said corresponding portions comprise a plurality of lugs on an outer surface of said first element and a plurality of openings on an inner surface of said second element, said openings being positioned to receive said lugs.

4. The dose indicating device of claim 3 wherein said openings comprise holes extending radially through said second element.

5. The dose indicating device of claim 2 wherein said indicator comprises a mechanical device.

6. The dose indicating device of claim 5 wherein said indicator comprises (a) a gear wheel mounted in said second element, (b) a digit display device having a plurality of digits displayed on its outer surface, said digit display device being rotatably mounted in operative engagement with said gear wheel and being positioned so that at least one of said digits is displayed in said display opening, and (c) a driving arm mounted on an inner wall of said first element and constructed to rotate the gear wheel when the first element is rotated, thereby rotating the digit display device to display a new digit in said display opening.

7. The dose indicating device of claim 6 wherein said digit display device comprises a digit wheel.

8. The dose indicating device of claim 6 wherein said digit display device comprises a digit tape mounted on a roller.

9. The dose indicating device of claim 6 wherein said digit display device comprises a digit disc and said gear wheel comprises a driving wheel having a plurality of steps.

10. The dose indicating device of claim 9 wherein said digit disc comprises a guiding path, and the dose indicating device further comprises an aperture disc disposed adjacent to the digit disc, said aperture disc having an aperture and a magnifier mounted in said aperture and being mounted to move along said guiding path when said first and second elements are rotated relative to each other.

11. The dose indicating device of claim 6 wherein said digit display device comprises an outer digit disc and an inner digit disc, each digit disc having a plurality of teeth, and said gear wheel is fixed to the first element and has teeth arranged to cooperate with the teeth on the inner digit disc to move the inner digit disc relative to the outer digit disc when the first element is rotated.

12. The dose indicating device of claim 1 wherein said indicator comprises an electronic device.

13. The dose indicating device of claim 12 wherein said indicator is positioned in the inhalation channel and comprises a microphone, a battery, a microprocessor and a microswitch.

14. The dose indicating device of claim 13 wherein said microphone is constructed to detect a "click" sound which is created when the maneuvering element is rotated, and said first element includes a lug positioned to activate the microswitch when the first element is rotated.

15. The dose indicating device of claim 1 wherein said first element includes markings for indicating whether the maneuvering element has been rotated sufficiently to load the dose of the medicament to the dosing unit.

16. The dose indicating device of claim 1 wherein said dose indicating device is constructed for use with a dry-powder, breath-actuated inhalator.

17. The dose indicating device of claim 1 wherein said dose indicating device is constructed for use with an inhalator that is constructed to deliver a medicament to a bronchial area of the user.

* * * * *